| United States Patent [19] | [11] Patent Number: 4,906,748 |
| Ashizawa et al. | [45] Date of Patent: Mar. 6, 1990 |

[54] CEPHEM DERIVATIVE CRYSTALS

[75] Inventors: Kazuhide Ashizawa; Kiyohiko Uchikawa, both of Ibaraki; Tadashi Sato, Chiba; Yasuo Ishibashi, Gifu, all of Japan

[73] Assignee: Eisai Co., Ltd., Tokyo, Japan

[21] Appl. No.: 224,122

[22] Filed: Jul. 11, 1988

[30] Foreign Application Priority Data

Jul. 9, 1987 [JP] Japan ................................. 62-169817
Jul. 9, 1987 [JP] Japan ................................. 62-169818

[51] Int. Cl.$^4$ .................... C07D 501/46; A61K 31/54
[52] U.S. Cl. .................................................. 540/222
[58] Field of Search ................. 540/225, 222, 226, 227

[56] References Cited

U.S. PATENT DOCUMENTS 4,748,171 5/1988 Yamauchi et al. .................. 540/222

Primary Examiner—Nicholas S. Rizzo
Attorney, Agent, or Firm—Wenderoth, Lind & Ponack

[57] ABSTRACT

Disclosed herein are 7β-[(Z)-2-(5-amino-1,2,4-thiadiazol-3-yl)-2-methoxyiminoacetamido]-3-(4-carbamoyl-1-quinuclidinio)methyl-3-cephem-4-carboxylate crystals comprising X-ray diffraction pattern possessing the characteristic diffraction intensity at the spacing d (unit: angstrom) shown in the following (i), (ii) or (iii):
(i): 6.2, 5.1 and 5.0;
(ii): 10.6, 5.3 and 5.1;
(iii): 15.4, 5.0 and 4.6.

A process for the preparation of the crystals is also disclosed.

9 Claims, No Drawings

CEPHEM DERIVATIVE CRYSTALS

BACKGROUND OF THE INVENTION

1. Filed of the Invention:

The present invention relates to a cephem derivative having a specific crystal structure and a process for the preparation thereof.

2. Description of the Related Art:

7β-[(Z)-2-(5-Amino-1,2,4-thiadiazol-3-yl)-2-methoxyiminoacetamido]-3-(4-carbamoyl-1-quinuclidinio)-methyl-3-cephem-4-carboxylate and its possession of excellent antimicrobial activity are described in Japanese Patent Laid-Open No. 123,189/1987. That described in the same disclosure is however an amorphous substance or type I crystals. The compound of the amorphous form is obtained by a method such as freeze drying of its corresponding solution, rapid distilling-off of its solvent, rapid deposition of the compound by addition of a poor solvent, or the like. On the other hand, the type I crystals are obtained by crystallizing out from an ethanol-water mixed solvent. Of those, the type I crystals is very poor in stability in that the residual rate of the compound when stored (in a hermetically sealed container) at room temperature for 1 month is 50% or lower. Although the amorphous compound is better in stability than the type I crystals, its residual rate when stored (in a hermetically sealed container) at room temperature for 6 months is 90% or lower. Therefore, it cannot be said that the amorphous compound has sufficient stability.

SUMMARY OF THE INVENTION

With the foregoing in view, the present inventors have carried out an extensive investigation. As a result, it has been found that a compound having a specific crystal form (type III, type IV or type VI) has excellent stability, leading to completion of this invention.

In an aspect of the invention, there is thus provided crystals of the above-mentioned compound, which have excellent stability, and a preparation process thereof.

The above and other objects, features and advantages of the present invention will become apparent from the following description and the appended claims.

DETAILED DESCRIPTION OF THE INVENTION

The compound according to this invention is 7β-[(Z)-2-(5-amino-1,2,4-thiadiazole-3-yl)-2-methoxyiminoacetamido]-3-(4-carbamoyl-1-quinuclidinio)-methyl-3-cephem-4-carboxylate:

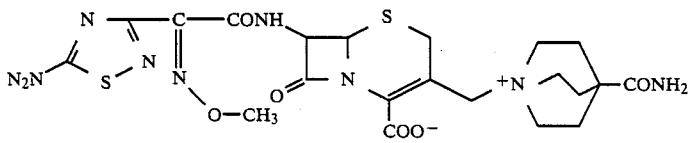

having the following crystal structure:

(1) 7β-[(Z)-2-(5-Amino-1,2,4-thiadiazol-3-yl)-2-methoxyiminoacetamido]-3-(4-carbamoyl-1-quinuclidinio)methyl-3-cephem-4-carboxylate crystals (hereinafter called "type III crystals") comprising X-ray diffraction pattern possessing the characteristic diffraction intensity at the spacing d of 6.2, 5.1 and 5.0 (unit: angstrom) as measured by X-ray diffraction;

(2) 7β-[(Z)-2-(5-Amino-1,2,4-thiadiazol-3-yl)-2-methoxyiminoacetamido]-3-(4-carbamoyl-1-quinuclidinio)methyl-3-cephem-4-carboxylate crystals (hereinafter called "type IV crystals") comprising X-ray diffraction pattern possessing the characteristic diffraction intersity at the spacing d of 10.6, 5.3 and 5.1 (unit: angstrom) as measured by X-ray diffraction; or (3) 7β-[(Z)-2-(5-Amino-1,2,4-thiadiazol-3-yl)-2-methoxyiminoacetamido]-3-(4-carbamoyl-1-quinuclidinio)methyl-3-cephem-4-carboxylate crystals (hereinafter called "type VI crystals") comprising X-ray diffraction pattern possessing the characteristic diffraction intensity at the spacing d of 15.4, 5.0 and 4.6 (unit: angstrom) as measured by X-ray diffraction.

More particularly, the above type III crystals have the following X-ray diffraction pattern:

The spacing d (unit: angstrom):

| | | | | |
|---|---|---|---|---|
| 13.3 | 11.2 | 8.2 | 7.8 | 7.3 |
| 6.7 | 6.5 | 6.2 | 6.0 | 5.6 |
| 5.4 | 5.1 | 5.0 | 4.8 | 4.7 |
| 4.5 | 4.4 | 4.3 | 4.1 | 4.0 |
| 3.9 | 3.7 | 3.6 | 3.5 | 3.4 |
| 3.3 | 3.2. | | | |

Among these spacing d, there are shown the characteristic (strong) diffraction intensity at the spacing d of 6.2, 5.1 and 5.0 (unit: angstrom).

The type IV crystals have the following X-ray diffraction pattern:

The spacing d (unit: angstrom):

| | | | | |
|---|---|---|---|---|
| 15.9 | 12.4 | 10.6 | 7.6 | 6.6 |
| 6.4 | 5.9 | 5.7 | 5.3 | 5.1 |
| 4.7 | 4.6 | 4.3 | 4.0 | 3.9 |
| 3.6 | 3.5 | 3.4 | 3.2 | 3.1. |

Among these spacing d, there are shown the characteristic (strong) diffraction intensity at the spacing d of 10.6, 5.3 and 5.1 (unit: angstrom).

The type VI crystals have the following X-ray diffraction pattern:

The spacing d (unit: angstrom):

| | | | | |
|---|---|---|---|---|
| 15.4 | 12.2 | 10.0 | 9.5 | 7.7 |
| 7.2 | 6.8 | 6.5 | 6.1 | 5.8 |
| 5.7 | 5.4 | 5.2 | 5.0 | 4.8 |
| 4.6 | 4.4 | 4.2 | 3.9 | 3.8 |
| 3.5 | 3.4 | 3.3 | 3.1 | 3.0. |

Among these spacing d, there are shown the characteristic (strong) diffraction intensity at the spacing d of 15.4, 5.0 and 4.6 (unit: angstrom).

The crystals according to this invention, which comprise X-ray diffraction pattern possessing the characteristic diffraction intensity at the spacing d (unit: angstrom) shown in the following (i), (ii) or (iii), can be prepared by crystallizing out 7β-[(Z)-2-(5-amino-1,2,4-thiadiazol-3-yl)-2-methoxyiminoacetamido]-3-(4-carbamoyl-1-quinuclidinio)methyl-3-cephem-4-carboxylate from a mixed solvent of water and methanol and then drying the same so that the water content may be decreased to 30% (W/W) or less.

(i): 6.2, 5.1 and 5.0;
(ii): 10.6, 5.3 and 5.1; or
(iii): 15.4, 5.0 and 4.6.

Each preparation process of the type III, type IV and type VI crystals according to this invention will hereinafter be described.

The type III crystals according to this invention can be obtained by the following method.

Namely, they are obtained by crystallizing out 7β-[(Z)-2-(5-amino-1,2,4-thiadiazol-3-yl)-2-methoxyiminoacetamido]-3-(4-carbamoyl-1-quinuclidinio)-methyl-3-cephem-4-carboxylate (hereinafter called "raw compound") from a mixed solvent of water and methanol and then drying the same so that the water content may be decreased to 5% (W/W) or less.

Although the type III crystals can be obtained under the conditions described above, it is desirable from the viewpoint of stability that their water content becomes less.

A mixed solvent containing methanol in an amount of 0.1 to 15 parts (V) per one part (V) of water is preferably used as the mixed solvent of water and methanol. The crystallization temperature is preferably in a range of from $-10°$ C. to $20°$ C. It is possible to use vacuum drying, vacuum freeze drying or the like as a drying means.

Although the type III crystals are very stable in dry state, they are not very good in stability under an atmosphere of high humidity. Accordingly, it is suitable to store them under hermetic conditions. In general, antimicrobial agents suitable for use in injecting are hermetically sealed in vials to be sold. Therefore, when the type III crystals are employed in such a case, they exhibit excellent stability. It is possible to obtain products by preparing the type III crystals according to this invention in a vial and then hermetically sealing them, as is.

The type IV and type VI crystals according to this invention can be obtained by the following method.

Namely, they are separately obtained by crystallizing out 7β-[(Z)-2-(5-amino-1,2,4-thiadiazol-3-yl)-2-methoxy-iminoacetamido]-3-(4-carbamoyl-1-quinuclidinio)methyl-3-cephem-4-carboxylate (hereinafter called "raw compound") from a mixed solvent of water and methanol and then drying the same so that their water contents may be decreased to 6–30% (W/W).

The type IV crystals are primarily obtained by drying crystals deposited until their water content is decreased to 6–17% (W/W) with 10–14% (W/W) being especially preferred. On the other hand, the type VI crystals are mainly obtained by drying the crystals deposited until their water content is decreased to 18–30% (W/W) with 22–26% (W/W) being especially preferred. When their water contents are decreased to 5% (W/W) or less, other crystals (type III) are primarily obtained. Crystals having a water content of 31% (W/W) and more tend to deliquesce.

A mixed solvent containing methanol in an amount of 0.1 to 15 parts (V) per part (V) of water is preferably used as the mixed solvent of water and methanol. The crystallization temperature is preferably in a range of from $-10°$ C. to $20°$ C. It is possible to use vacuum drying, air drying or the like as a drying means.

The type IV or type VI crystals according to this invention exhibit excellent chemical stability even when they are allowed to stand in a room or the like, or are stored in unsealed containers. The type IV crystals are stable under low-humidity conditions (humidity: about 35%) while the type VI crystals are stable under both low-humidity conditions (humidity: about 35%) and high-humidity conditions (humidity: about 85%) (although the type VI crystals are gradually converted into the type IV crystals under the low-humidity conditions, they are still stable chemically), By the way, although the type III crystals are very superior in stability to the type IV and type VI crystals in dry state (in a closed container), they are inferior in stability to the type IV and type VI crystals of this invention under conditions that a humidity is considerably high (about 20% or higher).

Therefore, the type IV and type VI crystals according to this invention are excellent as the form of storage where it is difficult to store in dry state, for example, upon the preparation of medicinal raw powders.

EXAMPLES

The present invention will hereinafter be described in further detail by Examples. However, this invention is not necessarily limited thereto.

EXAMPLE 1

One gram of a raw compound was placed in a 10-ml vial and 4 ml of distilled water was then added to dissolve the raw compound therein. Thereafter, 5 ml of methanol was added thereto, followed by storage of the resultant solution at $3°$ C. for 12 hours to crystallize out the raw compound. After the thus-obtained crystals were refrigerated to $-40°$ C., they were vacuum-dried for 40 hours while maintaining their temperature at $0°$ C. or lower. The crystals were then vacuum-dried for 20 hours while raising their temperature to $25°$ C., thereby obtaining type III crystals [water content: 1.03% (W/W)]. The vial containing the type III crystals was hermetically stoppered under dry nitrogen. The thus-obtained type III crystals had the following X-ray diffraction pattern:

| No. | Spacing d (angstrom) | Relative intensity $(I/I_o)$ |
| --- | --- | --- |
| 1 | 13.3 | 13 |
| 2 | 11.2 | 23 |
| 3 | 8.2 | 46 |
| 4 | 7.8 | 11 |
| 5 | 7.3 | 15 |
| 6 | 6.7 | 17 |
| 7 | 6.5 | 24 |
| 8 | 6.2 | 79 |
| 9 | 6.0 | 13 |
| 10 | 5.6 | 39 |
| 11 | 5.4 | 34 |
| 12 | 5.1 | 72 |
| 13 | 5.0 | 100 |
| 14 | 4.8 | 24 |
| 15 | 4.7 | 23 |
| 16 | 4.5 | 34 |
| 17 | 4.4 | 46 |
| 18 | 4.3 | 47 |
| 19 | 4.1 | 29 |
| 20 | 4.0 | 20 |
| 21 | 3.9 | 37 |
| 22 | 3.7 | 50 |
| 23 | 3.6 | 21 |
| 24 | 3.5 | 38 |
| 25 | 3.4 | 25 |
| 26 | 3.3 | 25 |

| No. | Spacing d (angstrom) | Relative intensity (I/I$_o$) |
| --- | --- | --- |
| 27 | 3.2 | 26 |

The type III crystals also had the following NMR spectrum (δ, D$_2$O): 2.3(6H, m), 3.5–4.0 (8H, m), 4.2(3H, s), 5.45(1H, d, J=6 Hz), 5.97(1H, d, J=6 Hz).

EXAMPLE 2

Type III crystals [water content: 0.9% (W/W)] were obtained in the same manner as in Example 1 except that 3 ml of water and 4 ml of methanol were used. Their X-ray diffraction pattern and NMR spectrum were the same as those in Example 1.

EXAMPLE 3

After 100 g of a raw compound was dissolved in 450 ml of distilled water and 600 ml of methanol was added thereto, the resultant solution was poured in portions into 100 vials of 10 ml each. The vials were stored at 3° C. for 18 hours to crystallize out the raw compound. After the thus-obtained crystals were refrigerated to −40° C., they were vacuum-dried for 40 hours while maintaining their temperature at 0° C. or lower. The crystals were then vacuum-dried for 15 hours while raising their temperature to 25° C., thereby obtaining type III crystals [water content: 1.40% (W/W)]. Each of the vials containing the type III crystals was hermetically stoppered under dry nitrogen. Their X-ray diffraction pattern and NMR spectrum were the same as those in Example 1.

EXAMPLE 4

After 100 g of a raw compound was dissolved in 350 ml of distilled water and 400 ml of methanol was added thereto, the resultant solution was poured in portions into 100 vials of 10 ml each. The vials were stored at 3° C. for 12 hours to crystallize out the raw compound. The thus-obtained crystals were vacuum-dried in the same manner as in Example 3, thereby obtaining type III crystals [water content: 1.31% (W/W)]. Their X-ray diffraction pattern and NMR spectrum were the same as those in Example 1.

EXAMPLE 5

Type III crystals were separately obtained in the same manner as in Example 1 except that the ratio (W/W/W) of the raw compound, distilled water and methanol in Example 1 was changed as described below. Their X-ray diffraction patterns and NMR spectra were the same as those in Example 1.

| Ratio of raw compound/ distilled water/methanol (W/W/W) | Water content of type III crystals obtained % (W/W) |
| --- | --- |
| 1/3/3 | 0.92 |
| 1/4/3.8 | 0.76 |
| 1/5/4.6 | 1.48 |
| 1/3/3.8 | 1.22 |
| 1/4/5.1 | 2.30 |
| 1/5/5.8 | 1.44 |
| 1/3/1.8 | 1.52 |
| 1/3.7/2.4 | 1.01 |
| 1/4/2.8 | 0.88 |
| 1/4/3.5 | 2.40 |
| 1/5/3.2 | 3.80 |

EXAMPLE 6

After 100 g of a raw compound was dissolved in 450 ml of distilled water and 450 ml of methanol was added thereto, the resultant solution was left over for 12 hours at 5° C. Crystals deposited were recovered by filtration and then washed with methanol, which had been refrigerated to −20° C. After the thus-washed crystals were dried over night under an atmosphere of 5° C. and 80% RH, they were charged in portions into 100 vials of 10 ml each of then vacuum-dried, thereby obtaining type III crystals [water content: 0.93% (W/W)]. Their X-ray diffraction pattern and NMR spectrum were the same as those in Example 1.

EXAMPLE 7

Type III crystals were separately obtained in the same manner as in Example 6 except that the ratio (W/W/W) of the raw compound, distilled water and methanol was changed as described below. Both X-ray diffraction patterns and NMR spectra were the same as those in Example 1.

| Ratio of raw compound/ distilled water/methanol (W/W/W) | Water content of type III crystals obtained % (W/W) |
| --- | --- |
| 1/4.5/4 | 4.8 |
| 1/4.5/4.5 | 3.53 |
| 1/4/5 | 2.13 |
| 1/4/4.5 | 4.95 |

Effects of the Invention

The individual type III crystals obtained in accordance with the present invention were hermetically sealed in containers under an atmosphere of dry nitrogen to test their chemical stability. Namely, the residual rate of the compound was determined by analyzing the samples after the storage by high performance liquid chromatography. As controls, both type I crystals and amorphous substance were used. The samples used in the test were prepered in the following manner.

Type III crystals: Type III crystals obtained in the same manner as in Example 1 were hermetically sealed in containers under an atmosphere of dry nitrogen.

Type I crystals: A sixfold amount (V) of ethanol was added to a 20% (W/W) aqueous solution of the raw compound and the resultant solution was stored at 5° C. for 12 hours. After crystals deposited were recovered by filtration and then washed with ethanol cooled, they were air-dried at room temperature [water content: 26.2% (W/W)]. The thus-dried crystals were hermetically sealed in containers under an atmosphere of dry nitrogen.

Amorphous substance: A 20% (W/W) aqueous solution of the raw compound was subjected to vacuum freeze drying [water content: 0.9% (W/W)]. The thus-dried substance was hermetically sealed in containers under an atmosphere of dry nitrogen.

| | | Chemical stability | | |
| --- | --- | --- | --- | --- |
| | | Residual rate (%) | | |
| Conditions stored | | Type III crystals | Type I crystals | Amorphous substance |
| 1 month | 25° C. | 99.4 | 48.3 | 95.3 |
| | 40° C. | 97.6 | 0.0 | 85.7 |
| | 50° C. | 95.0 | — | 77.7 |

-continued

| Conditions stored | | Chemical stability | | |
|---|---|---|---|---|
| | | Residual rate (%) | | |
| | | Type III crystals | Type I crystals | Amorphous substance |
| | 60° C. | 91.2 | — | 68.3 |
| 3 months | 25° C. | 99.0 | 0.6 | 91.1 |
| | 40° C. | 94.5 | — | 77.8 |
| | 50° C. | 91.8 | — | 66.5 |
| | 60° C. | 85.8 | — | 54.7 |
| 6 months | 25° C. | 97.8 | 0.0 | 87.3 |
| | 40° C. | 93.8 | — | 68.9 |

As described above, the type III crystals according to this invention are excellent in stability compared with the type I crystals and amorphous substance.

EXAMPLE 8

One gram of a raw compound was dissolved in 4 ml of distilled water and 5 ml of methanol was added thereto. After storing the resultant solution at 3° C. for 12 hours, crystals deposited were recovered by filtration. The thus-recovered crystals were washed with a 90% (V/V) aqueous solution of methanol, which had been refrigerated to −20° C. The thus-washed crystals were dried over night under an atmosphere of room temperature and 36% RH, thereby obtaining type IV crystals [water content: 12.4% (W/W)].

The thus-obtained type IV crystals had the following X-ray diffraction pattern:

| No. | Spacing d (angstrom) | Relative intensity ($I/I_o$) |
|---|---|---|
| 1 | 15.9 | 23 |
| 2 | 12.4 | 40 |
| 3 | 10.6 | 75 |
| 4 | 7.6 | 49 |
| 5 | 6.6 | 55 |
| 6 | 6.4 | 32 |
| 7 | 5.9 | 44 |
| 8 | 5.7 | 32 |
| 9 | 5.3 | 95 |
| 10 | 5.1 | 100 |
| 11 | 4.7 | 72 |
| 12 | 4.6 | 41 |
| 13 | 4.3 | 55 |
| 14 | 4.0 | 53 |
| 15 | 3.9 | 51 |
| 16 | 3.6 | 33 |
| 17 | 3.5 | 31 |
| 18 | 3.4 | 55 |
| 19 | 3.2 | 34 |
| 20 | 3.1 | 34 |

The type IV crystals also had the following NMR spectrum ($\delta$, $D_2O$): 2.3(6H, m), 3.5–4.0(8H, m), 4.2(3H, s), 5.45(1H, d, J=6 Hz), 5.97(1H, d, J=6 Hz).

EXAMPLE 9

One gram of a raw compound was dissolved in 5 ml of distilled water and 5 ml of methanol was added thereto. After storing the resultant solution at 0° C. for 12 hours, crystals deposited were recovered by filtration. The thus-recovered crystals were washed with methanol, which had been refrigerated to −20° C. The thus-washed crystals were dried over night under an atmosphere of room temperature and 30% RH, thereby obtaining type IV crystals [water content: 11.8% (W/W)]. Their X-ray diffraction pattern and NMR spectrum were the same as those in Example 8.

EXAMPLE 10

One hundred grams of a raw compound were dissolved in 450 ml of distilled water and 600 ml of methanol was added thereto. After storing the resultant solution at 3° C. for 18 hours, crystals deposited were recovered by filtration. The thus-recovered crystals were washed with methanol, which had been refrigerated to −20° C. The thus-washed crystals were dried over night under an atmosphere of room temperature and 40% RH, thereby obtaining type IV crystals [water content: 12.2% (W/W)]. Their X-ray diffraction pattern and NMR spectrum were the same as those in Example 8.

EXAMPLE 11

One hundred grams of a raw compound were dissolved in 350 ml of distilled water and 400 ml of methanol was added thereto. After storing the resultant solution at 3° C. for 12 hours, crystals deposited were recovered by filtration. The thus-recovered crystals were washed with methanol, which had been refrigerated to −20° C. The thus-washed crystals were dried over night under an atmosphere of room temperature and 35% RH, thereby obtaining type IV crystals [water content: 12.1% (W/W)]. Their X-ray diffraction pattern and NMR spectrum were the same as those in Example 8.

EXAMPLE 12

One gram of a raw compound was dissolved in 4 ml of distilled water and 5 ml of methanol was added thereto. After storing the resultant solution at 3° C. for 12 hours, it was refrigerated to −40° C. Crystals deposited were vacuum-dried so as to give a water content of 12.2% (W/W) while maintaining their temperature at 0° C. or lower. Their X-ray diffraction pattern and NMR spectrum were the same as those in Example 8.

EXAMPLE 13

One gram of a raw compound was dissolved in 4.5 ml of distilled water and 4.0 ml of methanol was added thereto. After allowing the resultant solution to stand at 5° C. for 10 hours, it was refrigerated to −40° C. Crystals deposited were vacuum-dried so as to give a water content of 6.8% (W/W) while maintaining their temperature at 0° C. or lower, thereby obtaining type IV crystals.

Type IV crystals were separately obtained in the same manner as described above except that the following proportions (W/W/W) of the raw compound, distilled water and methanol were used respectively.

| Ratio of raw compound/ distilled water/methanol (W/W/W) | Water content of type IV crystals obtained % (W/W) |
|---|---|
| 1/4/3.2 | 5.90 |
| 1/4/4.0 | 11.20 |
| 1/4/3.8 | 10.60 |

The X-ray diffraction patterns and NMR spectra of all the type IV crystals thus obtained were the same as those in Example 8.

EXAMPLE 14

One hundred grams of a raw compound were dissolved in 400 ml of water and 450 ml of methanol was added thereto. After storing the resultant solution at 3° C. for 15 hours, crystals deposited were recovered by filtration. The thus-recovered crystals were washed with methanol, which had been refrigerated to −20° C. The thus-washed crystals were dried over night under an atmosphere of room temperature and 35% RH, thereby obtaining type IV crystals [water content: 15.90% (W/W)]. Their X-ray diffraction pattern and NMR spectrum were the same as those in Example 8.

EXAMPLE 15

One gram of a raw compound was dissolved in 4 ml of water and 5 ml of methanol was added thereto. After storing the resultant solution at 3° C. for 12 hours, crystals deposited were recovered by filtration. The thus-recovered crystals were washed with a 90% aqueous solution of methanol, which had been refrigerated to −20° C. The thus-washed crystals were dried over night in a refrigerator (3° C., 75% RH), thereby obtaining type VI crystals [water content: 25.2% (W/W)].

The thus-obtained type IV crystals had the following X-ray diffraction pattern:

| No. | Spacing d (angstrom) | Relative intensity ($I/I_o$) |
|---|---|---|
| 1 | 15.4 | 100 |
| 2 | 12.2 | 43 |
| 3 | 10.0 | 20 |
| 4 | 9.5 | 18 |
| 5 | 7.7 | 19 |
| 6 | 7.2 | 24 |
| 7 | 6.8 | 18 |
| 8 | 6.5 | 17 |
| 9 | 6.1 | 26 |
| 10 | 5.8 | 23 |
| 11 | 5.7 | 21 |
| 12 | 5.4 | 31 |
| 13 | 5.2 | 51 |
| 14 | 5.0 | 65 |
| 15 | 4.8 | 44 |
| 16 | 4.6 | 73 |
| 17 | 4.4 | 28 |
| 18 | 4.2 | 48 |
| 19 | 3.9 | 36 |
| 20 | 3.8 | 37 |
| 21 | 3.5 | 28 |
| 22 | 3.4 | 47 |
| 23 | 3.3 | 33 |
| 24 | 3.1 | 37 |
| 25 | 3.0 | 32 |

The type VI crystals had the following NMR spectrum ($\delta$, $D_2O$): 2.3(6H, m), 3.5–4.0(8H, m), 4.2(3H, s), 5.45(1H, d, J=6 Hz), 5.97(1H, d, J=6 Hz).

EXAMPLE 16

One gram of a raw compound was dissolved in 5 ml of water and 5 ml of methanol was added thereto. After storing the resultant solution at 0° C. for 12 hours, crystals deposited were recovered by filtration. The thus-recovered crystals were washed with methanol, which had been refrigerated to −20° C. The thus-washed crystals were dried over night under an atmosphere of room temperature and 84% RH, thereby obtaining type VI crystals [water content: 23.80% (W/W)]. Their X-ray diffraction pattern and NMR spectrum were the same as those in Example 15.

EXAMPLE 17

One hundred grams of a raw compound were dissolved in 450 ml of water and 600 ml of methanol was added thereto. After storing the resultant solution at 3° C. for 18 hours, crystals deposited were recovered by filtration. The thus-recovered crystals were washed with methanol, which had been refrigerated to −20° C. The thus-washed crystals were dried over night in a refrigerator (3° C., 75% RH), thereby obtaining type VI crystals [water content: 26.2% (W/W)]. Their X-ray diffraction pattern and NMR spectrum were the same as those in Example 15.

EXAMPLE 18

One hundred grams of a raw compound were dissolved in 350 ml of water and 400 ml of methanol was added thereto. After storing the resultant solution at 3° C. for 12 hours, crystals deposited were recovered by filtration. The thus-recovered crystals were washed with methanol, which had been refrigerated to −20° C. The thus-washed crystals were dried over night under an atmosphere of room temperature and 84% RH, thereby obtaining type VI crystals [water content: 29.2% (W/W)]. Their X-ray diffraction pattern and NMR spectrum were the same as those in Example 15.

EXAMPLE 19

One hundred grams of a raw compound were dissolved in 400 ml of water and 450 ml of methanol was added thereto. After allowing the resultant solution to stand at 3° C. for 15 hours, crystals deposited were recovered by filtration. The thus-recovered crystals were washed with methanol, which had been refrigerated to −20° C. The thus-washed crystals were dried over night under an atmosphere of 5° C. and 80% RH, thereby obtaining type VI crystals [water content: 19.3% (W/W)].

Under the same conditions as described above except for the drying time, typing VI crystals having water contents of 20.9 (W/W) and 26.2% (W/W) are separately obtained.

The X-ray diffraction patterns and NMR spectra of all the type VI crystals thus obtained were the same as those in Example 15.

Effects of the Invention

With regard to the type IV crystals and type VI crystals obtained in accordance with the present invention, their chemical stability under atmospheres of predetermined humidity was tested. Namely, the residual rate of the compound was determined by analyzing the samples after the storage by high performance liquid chromatography. As controls, both type I crystals and amorphous substance were used.

The samples used in the test were prepered in the following manner.

Type IV crystals: They were prepared in accordance with the procedure of Example 8.

Type VI crystals: They were prepared in accordacne with the procedure of Example 15.

Type I crystals: A sixfold amount (V) of ethanol was added to a 20% (W/W) aqueous solution of the raw compound and the resultant solution was stored at 5° C. for 12 hours. After crystals deposited were recovered by filtration and then washed with ethanol cooled, they were air-dried at room temperature [water content: 26.2% (W/W)].

Amorphous substance: A 20% (W/W) aqueous solution of the raw compound was subjected to vacuum freeze drying [water content: 0.9% (W/W)].

| Chemical stability (store at room temperature for 1 month) | | |
| --- | --- | --- |
|  | Residual rate (%) | |
|  | RH: 35% | RH: 85% |
| Type IV crystals | 99.3 | 92.6 |
| Type VI crystals | 99.1 | 100.1 |
| Type I crystals | 48.3 | Deliquesced |
| Amorphous substance | 54.1 | Deliquesced |

Having now fully described the invention, it will be apparent to one of ordinary skill in the art that many change and modification can be made thereto without departing from the spirit or scope of the invention as set forth herein.

What is claimed is:

1. 7β-[(Z)-2-(5-Amino-1,2,4-thiadiazol-3-yl)-2-methoxyiminoacetamido]-3-(4-carbamoyl-1-quinuclidinio)-methyl-3-cephem-4-carboxylate crystals comprising X-ray diffraction pattern possessing the characteristic diffraction intensity at the spacing d (unit: angstrom) shown in the following (i), (ii) or (iii):
   (i): 6.2, 5.1 and 5.0;
   (ii): 10.6, 5.3 and 5.1;
   (iii): 15.4, 5.0 and 4.6.

2. The crystals as claimed in claim 1, which have the following X-ray diffraction pattern:
The spacing d (unit: angstrom):

| 13.3 | 11.2 | 8.2 | 7.8 | 7.3 |
| --- | --- | --- | --- | --- |
| 6.7 | 6.5 | 6.2 | 6.0 | 5.6 |
| 5.4 | 5.1 | 5.0 | 4.8 | 4.7 |
| 4.5 | 4.4 | 4.3 | 4.1 | 4.0 |
| 3.9 | 3.7 | 3.6 | 3.5 | 3.4 |
| 3.3 | 3.2. | | | |

3. The crystals as claimed in claim 1, which have the following X-ray diffraction pattern:
The spacing d (unit: angstrom):

| 15.9 | 12.4 | 10.6 | 7.6 | 6.6 |
| --- | --- | --- | --- | --- |
| 6.4 | 5.9 | 5.7 | 5.3 | 5.1 |
| 4.7 | 4.6 | 4.3 | 4.0 | 3.9 |
| 3.6 | 3.5 | 3.4 | 3.2 | 3.1. |

4. The crystals as claimed in claim 1, which have the following X-ray diffraction pattern:
The spacing d (unit: angstrom):

| 15.4 | 12.2 | 10.0 | 9.5 | 7.7 |
| --- | --- | --- | --- | --- |
| 7.2 | 6.8 | 6.5 | 6.1 | 5.8 |
| 5.7 | 5.4 | 5.2 | 5.0 | 4.8 |
| 4.6 | 4.4 | 4.2 | 3.9 | 3.8 |
| 3.5 | 3.4 | 3.3 | 3.1 | 3.0. |

5. A process for the preparation of crystals comprising X-ray diffraction pattern possessing the characteristic diffraction intensity at the spacing d (unit: angstrom) shown in the following (i), (ii) or (iii), which comprises crystallizing out 7β-[(Z)-2-(5-amino-1,2,4-thiadiazol-3-yl)-2-methoxyiminoacetamido]-3-(4-carbamoyl-1-quinuclidinio)methyl-3-cephem-4-carboxylate from a mixed solvent of water and methanol and then drying the same so that the water content may be decreased to 30% (W/W) or less:
   (i): 6.2, 5.1 and 5.0;
   (ii): 10.6, 5.3 and 5.1;
   (iii): 15.4, 5.0 and 4.6.

6. The process for the preparation of the crystals comprising X-ray diffraction pattern possessing the characteristic diffraction intensity at the spacing d of 6.2, 5.1 and 5.0 (unit: angstrom) as claimed in claim 5, which comprises drying so that the water content may be decreased to 5% (W/W) or less.

7. The process for the preparation of the crystals comprising X-ray diffraction pattern possessing the characteristic diffraction intensity at the spacing d of 10.6, 5.3 and 5.1 (unit: angstrom) as claimed in claim 5, which comprises drying so that the water content may be decreased to 6-17% (W/W).

8. The process for the preparation of the crystals comprising X-ray diffraction pattern possessing the characteristic diffraction intensity at the spacing d of 15.4, 5.0 and 4.6 (unit: angstrom) as claimed in claim 5, which comprises drying so that the water content may be decreased to 18-30% (W/W).

9. The process for the preparation of the crystals as claimed in claim 5, wherein a mixed solvent containing methanol in an amount of 0.1 to 15 parts (V) per one part (V) of water is used as the mixed solvent of water and methanol, and the crystallization is effected at a temperature of −10° C. to 20° C.

* * * * *